United States Patent [19]
Lee et al.

[11] Patent Number: 6,064,474
[45] Date of Patent: May 16, 2000

[54] OPTICAL MEASUREMENT OF BLOOD HEMATOCRIT INCORPORATING A SELF-CALIBRATION ALGORITHM

[75] Inventors: Wylie I. Lee, Laguna Hills, Calif.; Jason E. Alderete, Hopkins; William V. Fowler, Minneapolis, both of Minn.

[73] Assignee: Optical Sensors, Inc., Eden Prairie, Minn.

[21] Appl. No.: 09/020,118

[22] Filed: Feb. 6, 1998

[51] Int. Cl.$^7$ .................................................. G01N 33/49
[52] U.S. Cl. ............................................................. 356/39
[58] Field of Search .......................................... 356/39, 70

[56] References Cited

U.S. PATENT DOCUMENTS

| | | | |
|---|---|---|---|
| 4,929,847 | 5/1990 | Yamazoe et al. | 356/70 |
| 5,048,524 | 9/1991 | Bailey | 128/634 |
| 5,372,136 | 12/1994 | Steuer et al. | 128/633 |
| 5,456,253 | 10/1995 | Steuer et al. | 128/633 |
| 5,553,615 | 9/1996 | Carim et al. | 128/633 |

FOREIGN PATENT DOCUMENTS

| | | | |
|---|---|---|---|
| 0 401 453 A1 | 12/1990 | European Pat. Off. | G01N 21/31 |
| 4-191642 | 7/1992 | Japan | G01N 21/49 |

OTHER PUBLICATIONS

Pittman et al., "Measurement of percent oxyhemoglobin in the microvasclature", *J. Appl. Physiol.* (1975) 38:321–327.

Shepherd et al., "Continuous spectrophotometric measurements of arteriovenous oxygen difference," *J. Appl. Physiol* (1975) 39:152–155.

Steinke et al., "Reflectance measurements of hematocrit and oxyhemoglobin saturation," *m J Physiol* (1987) 253: H147–H153.

Grover, "Improved Extracorporeal Reflectance Oximeter," *Conf. Proced. of the 26th Ann. Oonf. on Eng. in Med. and Biol.*, (1973).

Miyake et al., "The detection of cytochrome oxidase heme iron and copper absorption in the blood–perfused and blood–free brain in normoxia and hypoxia," *Anal Biochem,* (1991), 192:149–155.

Pittman et al., "A new method for the measurement of percent oxyhemoglobin," *J Appl Physiol* (1975), 38:315–320.

*Primary Examiner*—Richard A. Rosenberger
*Attorney, Agent, or Firm*—Michael A. Glenn

[57] ABSTRACT

An optical method for obtaining hematocrit values of blood uses the light transmittance properties of blood as a means of acquiring information about the blood sample. An algorithm is used to calculate the hematocrit value based on the absorbance spectra obtained at wavelengths of approximately 500 nm and 800 nm. These absorbance wavelengths are selected for their insensitivity to the oxygen saturation level of hemoglobin. Additionally, the algorithm has demonstrated insensitivity to plasma and other blood constituent scattering effects.

21 Claims, 7 Drawing Sheets

| % Oxygen | Hct truth | Hct calc.* | bias |
|---|---|---|---|
| 7 | 13 | 12.6 | -0.4 |
|   | 39 | 38.9 | -0.1 |
|   | 42 | 42.7 | 0.7 |
| 14 | 13 | 13.1 | 0.1 |
|   | 39 | 39.3 | 0.3 |
|   | 42 | 42.1 | 0.1 |
| 72 | 13 | 13.1 | 0.1 |
|   | 39 | 38.9 | -0.1 |
|   | 42 | 41.2 | -0.8 |
|   |   | average | 0.0 |

*Represents the average of two measurements

OPTICAL MEASUREMENT OF BLOOD HEMATOCRIT INCORPORATING A SELF-CALIBRATION ALGORITHM

BACKGROUND OF THE INVENTION

1. Technical Field

The invention relates to the determination of blood hematocrit via optical means. More particularly, the invention relates to a technique for the optical measurement of blood hematocrit that incorporates a self-calibration algorithm.

2. Description of the Prior Art

Blood hematocrit refers to the packed red blood cell volume of a whole blood sample. Plasma constitutes the remaining portion of the whole blood. Hematocrit can be measured directly in one of several ways, for example by spinning down the red blood cells (RBCs) in a capillary tube. Following centrifugation, the volume of the RBCs is measured.

With regard to the determination of hematocrit via optical means, it is well known that the transmission of light through red blood cells is complicated by scattering components from plasma. The scattering capabilities of plasma vary from person to person, thereby complicating the determination of hematocrit.

U.S. Pat. No. 5,499,627 (and U.S. Pat. No. 5,372,136) to Steuer et al describes methods and an apparatus for determining hematocrit noninvasively and transcutaneously using reflectance or transmission spectrophotometry.

The method may be applied for in vitro analysis of blood drawn from a patient. In one embodiment, two wavelengths near or at hemoglobin isobestic points, e.g. 805 nm and 905 nm, are used to eliminate the effects of variable blood oxygenation on light absorption. Scattering from interstitial fluid is determined by measuring absorbance at a third wavelength where scattering accounts for 25–50% of the total absorbance of blood, e.g. 1310 nm. The value of the scattering term is then used to correct the absorbance equations. The apparatus is designed for continuous noninvasive measurement through body tissue. The geometry of the emitters and sensors is critical and must be determined empirically.

U.S. Pat. No. 5,277,181 to Mendelson et al describes a method for the noninvasive measurement of hematocrit and hemoglobin content at one or more wavelengths. One wavelength, e.g. 815 nm, is selected for its nonabsorbance by plasma. A second wavelength, e.g. 950 nm, is selected for its absorbance by both hemoglobin and plasma. The scattered and absorbed light at the second wavelength is detected with two detectors, and is split into DC and AC components. The measurements are empirically correlated with hematocrit, and predictive equations are then developed to quantiate hematocrit from relative concentrations of hemoglobin and plasma in the samples. Therefore, this technique is not self calibrating.

U.S. Pat. No. 5,553,615 to Carim et al describes a method and apparatus for the noninvasive prediction of hematocrit in mammalian blood. The method and apparatus evaluates the wave form for peaks, valleys, DC averages, and pulsatile averages at each wavelength selected, and for each pulse in an optical train. Wavelengths are selected which meet various criteria. Two wavelengths suffice to satisfy such criteria, i.e.:

A wavelength where water absorbance is at or near a measurable peak, e.g. 1195–1207 nm;

At least one (preferably two) wavelength(s) in the isobestic region of hemoglobin, e.g. 805–857 nm;

A wavelength where absorbance of water>>absorbance of total hemoglobin, e.g. 1300–1315 nm; and A wavelength where absorbance of total hemoglobin>>absorbance of water, e.g. 630–680 nm.

Four equations are generated to approximate the effect of pulsatile flow. Statistical analysis is then used to determine the best coefficients form prediction of hematocrit. The selected equation is stored electronically and used to predict unknown hematocrit values.

U.S. Pat. No. 4,805,623 to Jöbsis discloses a general spectrophotometric method for quantitatively determining the concentration of a dilute component in a clear or strongly light scattering environment, together with a reference of known concentration in the same environment. Multiple absorption wavelengths are used in a spectral region in which the dilute and/or reference components exhibit absorption. The number of wavelength required is determined by the number of dilute and reference components in the environment, and by the scattering characteristics of the environment. The device includes a means for a self-calibrating system. Algorithms are derived by matrix solution of simultaneous absorption equations which include scattering factors. The technique is directed to determining a dilute component relative to a reference standard in a strongly light scattering environment and therefore requires the use of a reference standard.

U.S. Pat. No. 3,847,483 to Shaw et al disclosed an oximeter operating at two radiation wavelengths to measure oxygen saturation independently of hematocrit and hemoglobin concentration. There is no requirement that the wavelengths be near or at an isobestic point for hemoglobin. The device uses fiber optic light guides in a double lumen catheter.

U.S. Pat. No. 4,447,150 to Heinemann discloses a device and method for measuring blood characteristics, especially blood oxygen saturation levels. Fiber optics are used to couple the lights sources and photosensor.

U.S. Pat. No. 4,623,248 to Sperinde discloses a fiber optic catheter for supplying radiation to blood at multiple wavelengths and detecting the intensities of the radiation back scattered from the blood at each wavelength.

U.S. Pat. No. 4,776,340 to Moran et al discloses the use of differential geometry to determine hematocrit during diagnostic cardiovascular cathetization. Two optical paths are used for light transmission by optical fibers.

U.S. Pat. No. 5,048,524 to Bailey discloses an apparatus and method for measuring hematocrit in real time in vivo by directing light through a blood sample of known width and calculating the parameters based on a set of predetermined molecular extinction coefficients and optical scattering coefficients. The molecular extinction coefficients are computed for hemolyzed blood (i.e. oxygenated and reduced blood). The optical scattering coefficients are calculated at various wavelengths from the transmittance spectra of whole blood and hemoglobin. The apparatus uses multiple optical fibers to transmit light of preselected wavelengths from LEDs to the sample, and a single optical fiber to receive the light passed through the blood. The light passes from the transmitting fibers through the blood to the receiving fiber. None of the wavelengths are required to be isobestic for hemoglobin.

U.S. Pat. No. 5,061,632 to Shepherd et al discloses an oximeter that measures total hemoglobin concentration in whole blood and oxygen saturation. The oximeter includes a glass capillary tube for holding the blood sample, red and infrared LEDs, and fiber optic light guides.

U.S. Pat. No. 5,239,185 to Ito et al discloses a method and apparatus for measuring hemoglobin in whole blood. The method uses two sets of measuring wavelengths (e.g. 570 nm/572 nm and 660 nm/672 nm). The method is based on an analysis of differences between the rate of change in the intensity of transmitted light caused by light absorption as compared with light scattering.

U.S. Pat. No. 5,456,253 (and U.S. Pat. No. 5,351,686) to Steuer et al disclose the use of two wavelengths of light transmitted through a cuvette which includes a transducer in one the cuvette walls for varying a predetermined separation, responsive to pressure pulsation in the fluid being measured. This technique is used for measuring blood constituents during pulsatile blood flow.

U.S. Pat. No. 5,385,539 to Maynard discloses a system in which transmitted light is received by two detectors at two different distances from an emitting source. In this system, one detector is used to set the gain of the other detector.

U.S. Pat. No. 5,331,958 to Oppenheimer discloses the use of one light source and two detectors—one detector directly across from a source (a transmitted light detector), and the other detector at some distance from the first detector (the back scatter light detector). The back scattered light compensates for change in light beam geometry induced by changes in blood electrolyte composition.

U.S. Pat. No. 5,149,503 to Kohno et al discloses hematocrit measurement by the use of reflected light at two wavelengths. The first wavelength is applied at a first light radiation section, and the second wavelength is applied at second and third light radiation sections.

U.S. Pat. No. 5,066,859 (and U.S. Pat. No. 5,249,584) to Karkar et al disclose the back scatter measurement of two wavelengths of light, e.g. 660 nm and 805 nm.

U.S. Pat. No. 4,243,883 to Schwarzmann discloses the use of 800 nm light transmission through a transparent lumen.

PCT Publication No. WO 95/04266 discloses the multi-wavelength near IR interrogation of blood flowing through a measuring cuvette.

PCT Publication No. WO 93/13706 discloses a pulse oximetry method and apparatus for measurement of blood hematocrit. "[F] or a fixed sample thickness and optical configuration, the hematocrit of whole blood can be determined simply and rapidly by measuring the ratio of optical densities of samples at these two isobestic wavelengths [i.e. 800 nm and 1300 nm]." The method assumes that the sample thickness is only a few millimeters, such that the ratio of absorbance at 800 nm and 1300 nm is linearly dependent on hematocrit. The apparatus consists of LEDs which emit light at 830 nm and 1300 nm. The light is transmitted by a fiber bundle to a lens which expands and collimates the lights into a beam. The beam is transmitted through a cuvette containing the sample, and is collected by a single photodiode.

PCT Publication No. WO 93/06774 discloses a method and apparatus for determining hematocrit in blood passing through a blood circuit. The method uses light at two wavelengths, in which the second and first wavelengths are symmetrically disposed about the isobestic wavelength of oxy- and deoxy-hemoglobin (e.g. 810 nm and 830 nm). The reflected light is measured at a single distance from the light source. Hematocrit is calculated based on the approximation of the amount of reflected light at the isobestic wavelength. The method attempts to compensate for the fact that the LEDs may not emit light at the specific isobestic point desired. The apparatus includes an LED, a photodiode, and software for performing calculations. The blood is typically passed through a cuvette, the LED provides light to the blood through fiber optic cables, and the photodiode receives light through a fiber optic cable. The device uses from two to four light emitter fiber optic channels, one for each wavelength of measurement. These channels transmit the radiation through the window of the cuvette. A fourth channel is included in the fiber optic cable for receiving reflected radiation and transmitting it to a single photodetector. The preferred embodiment measures reflected light, but the use of transmitted light is also contemplated.

Pittman and Duling, J. Applied Physiology 38:315 (1975) discloses that the fractional oxygen saturation of hemoglobin in whole blood can be determined by correcting optical density measurements for light scattering, based on a well known theory of light absorption and scattering by particulate suspensions. In this theory, absorption and scattering are treated independently and are shown to be potentially separable.

Further, the reference discloses that the equation:

$$\text{Absorption} = \text{a Beer-Lambert term} + \text{a scattering term}, \quad (1)$$

is well known in the art.

The authors state that because the scattering term is a complicated function dependent on multiple factors, such as wavelength, hematocrit, path length, particle size, shape, and orientation, it is impossible to measure the scattering term. Thus, an experimental situation is required in which all of these quantities remain constant during measurement. The described method involves determining the absorbance of whole blood at two isobestic wavelengths, where the ratio of hemoglobin molar extinction coefficients is significantly different from unity, and under conditions where concentrations and path length are the same.

The two absorption equations can be solved for the value of the scattering term, under the assumption that the latter is independent of wavelength. A third non-isobestic wavelength is selected for measurement. The scattering term is then subtracted from the absorbance at this wavelength.

The reference discloses that, over the range 510 nm to 575 nm, the scattering term is independent of wavelength, and notes that previous studies had shown wavelength independence of scattering from 500 nm to 630 nm. The authors state that the method is probably valid for the red and infrared regions because appropriate isobestic (e.g. 586 nm, 815 nm) and measuring (e.g. 660 nm) wavelengths are present in this region and there are no large absorption bands that can lead to wavelength dependent scattering. The authors emphasize the importance of ensuring that all of the light transmitted through a turbid solution is collected and note that the method can be used to measure oxygen saturation of whole blood in cuvettes (0.01 cm thick) in vitro.

It would be advantageous to provide an optical technique for measuring blood hematocrit that is self calibrating and that accounts for variability in plasma scattering components.

SUMMARY OF THE INVENTION

The invention provides an optical method and probe for determining hematocrit of a blood sample. The method relies on the measurement of absorbance of whole blood in forward scattering at two isobestic wavelengths for hemoglobin, i.e. 506 nm and 805 nm.

Absorbance equations, herein have the form:

$$T_i = K \cdot Hct + S,$$

wherein:

$T_i$ is total absorbance at an isobestic wavelength;

K is a constant that includes the molar extinction coefficient Hb at that wavelength, the red blood cell scattering factor, and the path length;

Hct is hematocrit; and

S is the light scattering from blood plasma.

The equations from the two isobestic wavelengths can be solved for the Hct term using the algorithm:

$$Hct=(T_{i,1}-R*T_{i,2})/(K_1-R*K_2).$$

where R is the ratio of scattering from plasma measured with two isobestic wavelengths.

$R=S_1/S_2$, which can be empirically measured.

In those embodiments of the invention having a very narrow cell path, the value of R may essentially equal one. In such case, $K_1$ and $K_2$ may be combined into a new constant K. Thus, the equation becomes:

$$Hematocrit=(Absorbance_{805\ nm}-Absorbance_{506\ nm})/K,$$

where K is the cell constant for any particular probe being used to make the measurements.

The disclosed method is advantageous in that it does not require in vitro or in vivo calibration and can be implemented with a streamlined measurement probe. The probe comprises a polymer block that includes a light transmitting optical fiber, a light receiving optical fiber, a measurement cell, and optical filters for wavelengths of 805 nm and 506 nm.

The disclosed technique for hematocrit analysis is considered preferable to traditional methods due to the rapid determination and preservation of the sample. No centrifugation or sample preparation is required for analysis, thereby allowing immediate determination. Additionally, no cellular disruption or reagents are required, thereby leaving the blood sample undefective for return to the patient. Furthermore, the invention relies on the transmission of light through the blood sample, as opposed to the back scattering methods used in prior analysis techniques.

DETAILED DESCRIPTION OF THE INVENTION

The invention provides an optical method and probe for determining hematocrit of a blood sample. The method relies on the forward scattering measurement of absorbance of whole blood at two isobestic wavelengths for hemoglobin, i.e. 506 nm and 805 nm.

Absorbance equations herein have the form:

$$T_i=K\cdot Hct+S, \qquad (2)$$

wherein:

$T_i$ is total absorbance at an isobestic wavelength;

K is a constant that includes the molar extinction coefficient of hemoglobin at that wavelength, the red blood cell scattering factor, and the path length;

Hct is hematocrit; and

S is the light scattering from other plasma components.

Equation (2) can be solved for the Hct term using the algorithm:

$$Hct=(T_{i,1}-R*T_{i,2})/(K_1-R*K_2). \qquad (3)$$

where R is the ratio of plasma scattering measured by two wavelengths.

$$R=S_1/S_2 \qquad (4)$$

In those embodiments of the invention having a very narrow cell path, the value of R may essentially equal one. In such case, $K_1$ and $K_2$ may be combined into a new constant K. Thus, the equation becomes:

$$Hematocrit=(Absorbance_{805\ nm}-Absorbance_{506\ nm})/K, \qquad (5)$$

where K is the cell constant for any particular probe being used to make the measurements.

Figure 3:
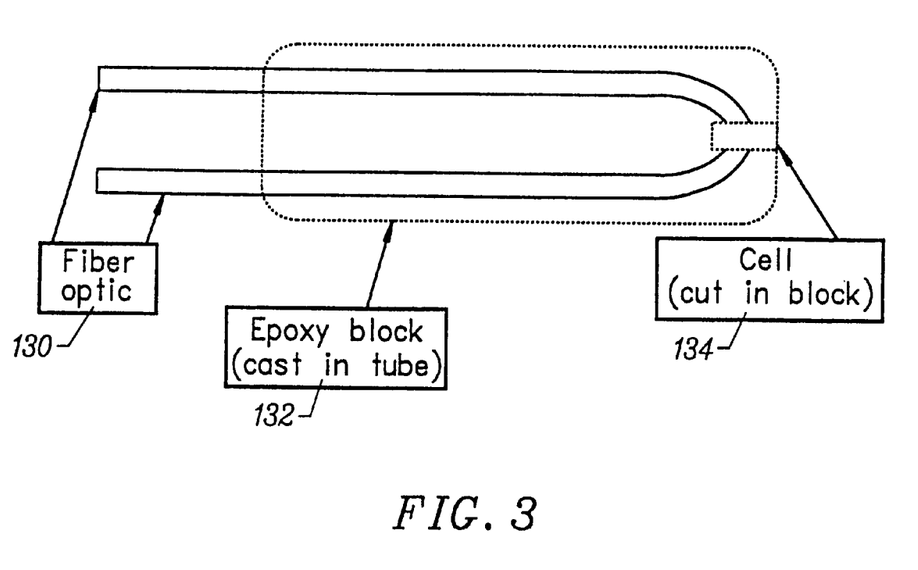
FIG. 3 is a block schematic diagram of a stick design probe according to the invention.

The disclosed method is advantageous in that it does not require in vitro or in vivo calibration and can be implemented with a streamlined measurement probe. The probe comprises a polymer block that includes a light transmitting optical fiber, a light receiving optical fiber, a measurement cell, and optical filters for wavelengths 805 nm and 506 nm (see FIGS. 3, 5 and 8, and the related discussion below).

The disclosed technique for hematocrit analysis is considered preferable to traditional methods due to the rapid determination and preservation of the sample. No centrifugation or sample preparation is required for analysis, thereby allowing immediate determination. Additionally, no cellular disruption or reagents are required, thereby leaving the blood sample undefiled for return to the patient. Furthermore, the invention relies on the transmission of light through the blood sample, as opposed to the back scattering methods used in prior analysis techniques.

Discussion

In a cuvette of fixed optical path length, L the intensity of transmitted light ($I_t$) can be expressed by Beer-Lambert's Law:

$$I_t=I_0*Exp\ (-T), \qquad (6)$$

where $I_0$ is the intensity of the incident light; and

T, known as absorption coefficient, is:

$$T=\{a*[HbO]+b*[Hb]+S_{RBC}+S_{plasma}\}*L \qquad (7)$$

wherein:

a and b are the molecular extinction coefficient of oxyhemoglobin and deoxyhemoglobin, $S_{RBC}$ is the forward scattering component from red blood cells, and $S_{plasma}$ is the forward scattering from the substances in blood plasma.

It can be assumed that:

$$S_{RBC}=S_c[RBC]=s*[tHb]. \qquad (8)$$

At isobestic wavelength, a=b=ai, therefore:

$$T_i=\{ai*[tHb]+s*[tHb]+S_{plasma}\}*L \qquad (9)$$

or $$T_i = (ai+s)*L*[tHb] + L*S_{plasma} \quad (10)$$

or, simply:

$$T_i = K*Hct + S. \quad (11)$$

Scattering from plasma is not a constant because of such factors as the variability in the individual's physical condition and diet. However, this variability in S can be compensated using the following algorithm. One can make the measurement with two lights of different isobestic wavelength, e.g. 805 nm and 506 nm.

With this algorithm:

$$T_{i,1} = K_1*Hct + S_1(i, 1=805 \text{ nm}) \quad (12)$$

and $$T_{i,2} = K_2*Hct + S_2(i, 2=506 \text{ nm}). \quad (13)$$

The ratio of scattering from plasma measured at two wavelengths can be empirically measured.

$$R = S_1/S_2. \quad (14)$$

Therefore, $$T_{i,1} = K_1*Hct + R*S_2 \quad (15)$$

and $$T_{i,2} = K_2*Hct + S_2 \quad (16)$$

Consequently, $$Hct = (T_{i,1} - R*T_{i,2})/(K_1 - R*K_2). \quad (17)$$

Because the values of R are close to 1.0 in empirical measurements with cells having small pathlengths, using the two isobestic wavelengths, one can further simplify the equation (17) to:

$$Hct = (T_{i,1} - T_{i,2})/K \quad (18)$$

where:

K is the cell constant.

It is thought that the donor-to-donor variability in plasma scattering may not be a significant factor in cells having a small pathlength. Presently preferred cell pathlengths are on the order of 175 to 250 microns. The preferred device uses this measurement algorithm and does not require any in vitro or in vivo calibration.

Trial 1

Figure 1:
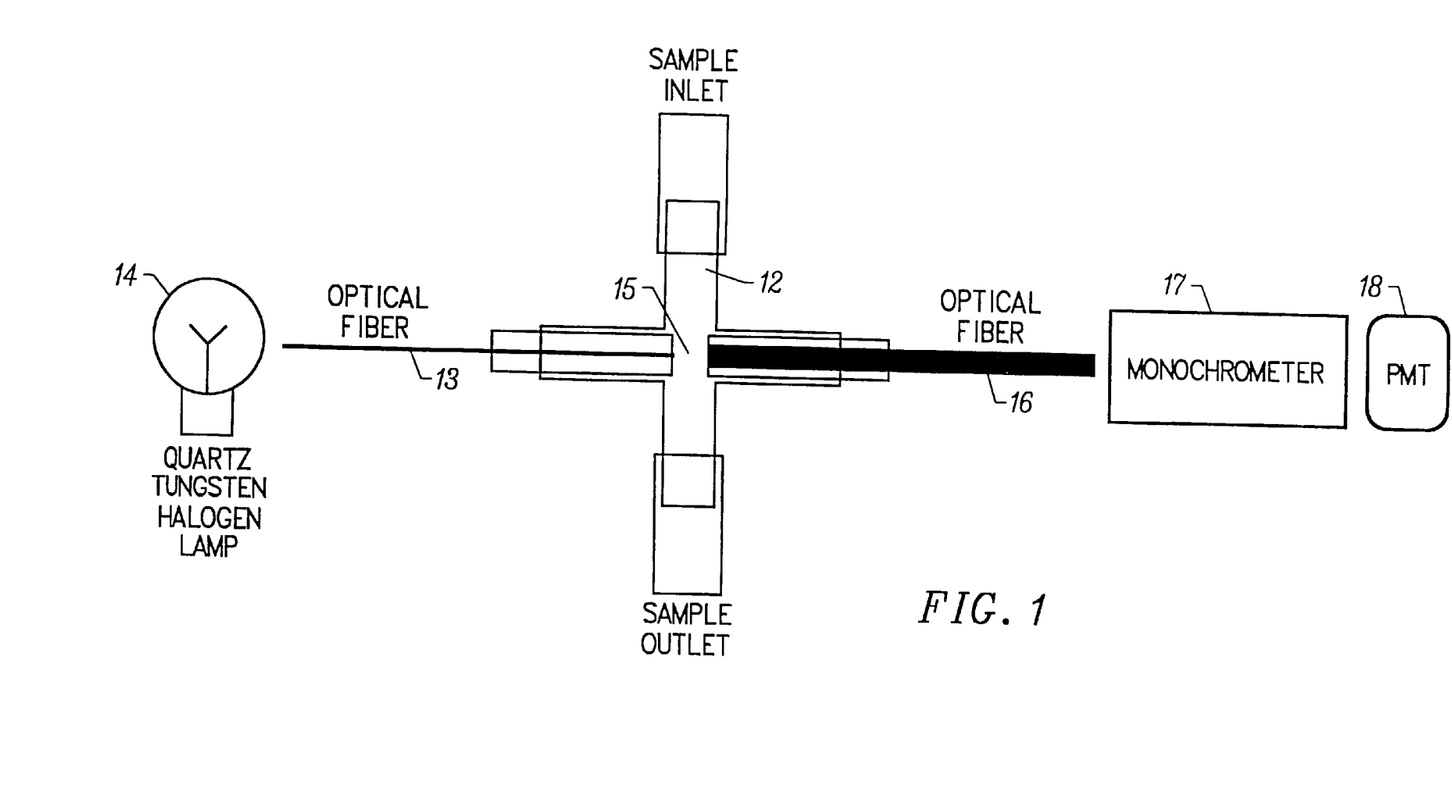
FIG. 1 is a block schematic diagram of a flow cell for absorbance measurements according to the invention.

This experiment used the spectrometer and detector in the Spex spectrofluorometer for data acquisition. A cell was constructed with a 4-way plastic tee 12 (FIG. 1). A 200 micron fiber 13 was used to guide light from a quartz-tungsten-halogen lamp 14 to the sample area 15. A 200 micron fiber 16 was used to guide sample-transmitted light to a monochrometer/PMT 17/18. Samples were introduced into the cell described above (see FIG. 1). The purpose of this experiment was to obtain the constants $R_1$, $K_1$, and $K_2$, described in the above algorithm (see Equation (17)).

Fresh bovine blood was centrifuged and the plasma was carefully removed to obtain fresh bovine plasma. The packed red blood cells (RBC's) were diluted with the plasma to obtain three blood samples with different hematocrit levels. The samples were analyzed for hematocrit on a Corning model 855 analyzer with a model 800 CO-oximeter attached. The optical cell was placed on a rocking plate (~25 Hz) to minimize settling of the RBC's during scanning. Scans were obtained for saline, plasma, and three blood hematocrit levels. The saline scan was used to calculate absorbance profiles for the other four samples.

Figure 2:
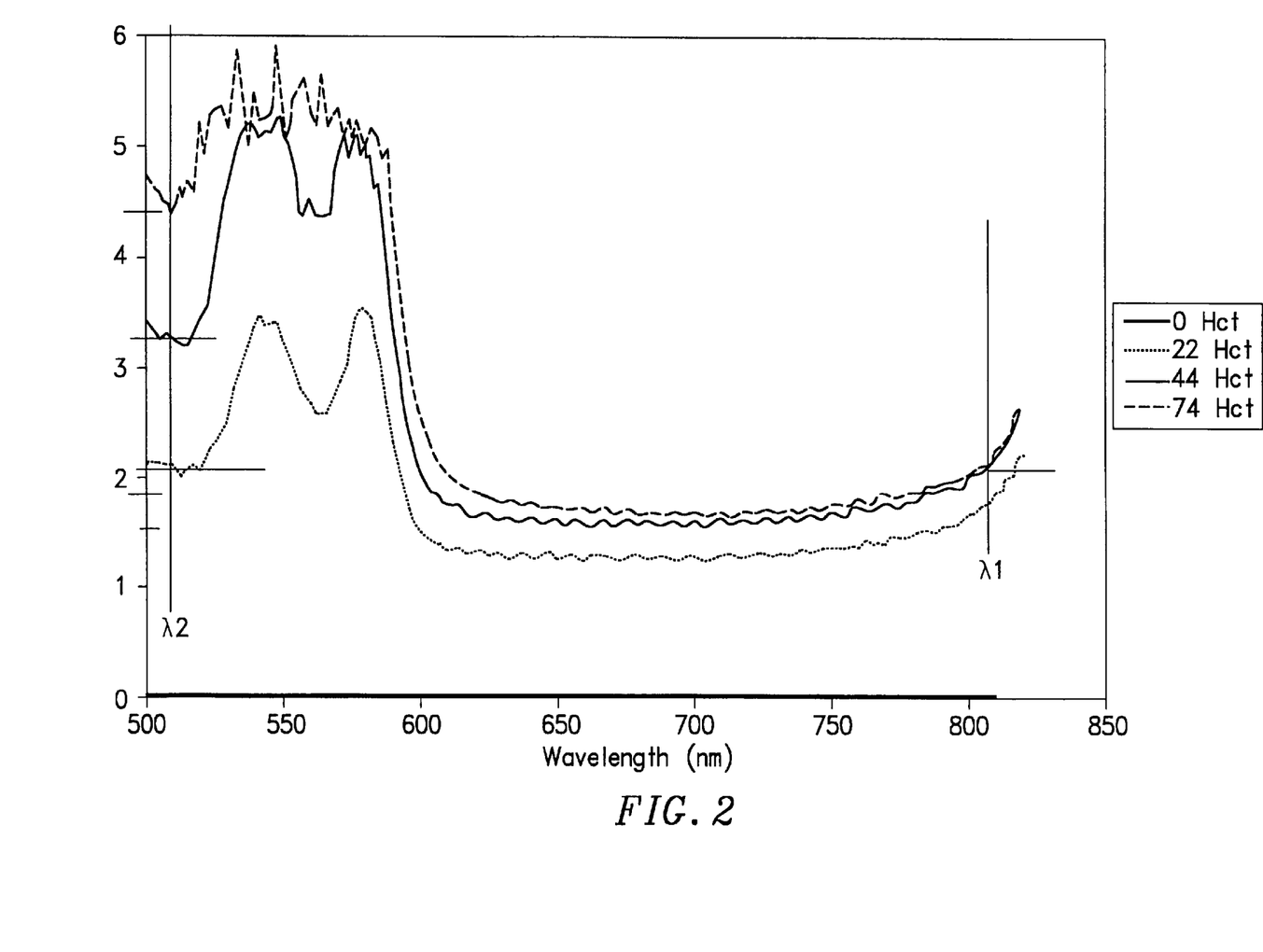
FIG. 2 is a graph that plots wavelength vs. absorbance for bovine blood during a first trial according to the invention.

The results are shown in FIG. 2. Using the data from the plasma scan, the R value obtained is 2.17. Further data analysis employed the curve-fitting program TableCurve 3D. Using TableCurve 3D (Version 1.03, Jandel Scientific), the values of $K_1$ and $K_2$ were 1.53 and 0.756, respectively, with an Fstat value of 110. Allowing the R value to be calculated from the program gave an R value of 1.28, with $K_1$ and $K_2$ values of 1.14 and 0.924 (the Fstat value for this fit was 849).

Trial 2

Figure 4:
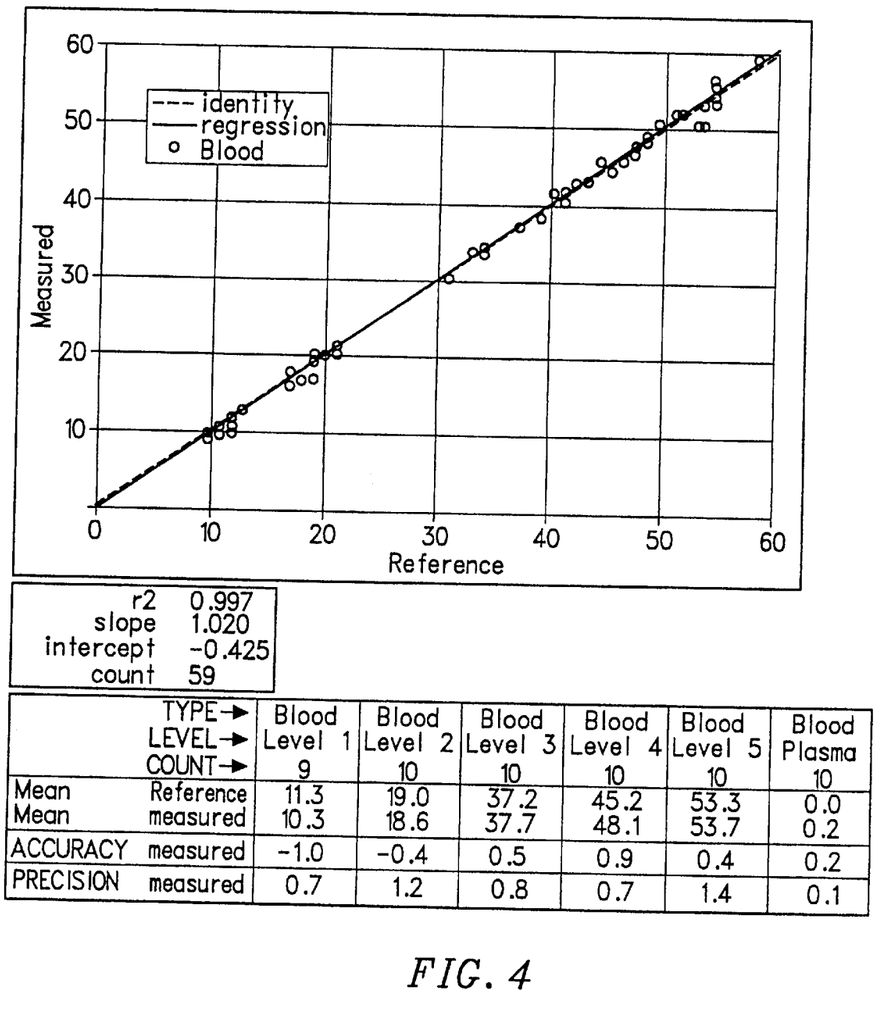
FIG. 4 is a graph plotting measured hematocrit values vs. reference hematocrit values according to a second trial.

Blood from ten different bovine was used in this experiment. The blood received contained heparin at 1000 U/ml. With each blood sample obtained, a portion of the blood was spun in a centrifuge to provide packed RBC's and plasma. The RBC's and plasma were then recombined with whole blood to obtain a range of hematocrit values. Reference values were obtained on a Ciba-Corning 855 with CO-oximeter. Coefficients used in the algorithm were obtained using the initial sample and were maintained for all subsequent samples. Instrumentation was a modified Optical Sensors ABG module fitted with a stick-design probe (see FIG. 3). The probe includes a pair of optical fibers 130 set in a cast epoxy block 132 in which a cell 134 is cut. The optical fibers are positioned such that their ends face each other on either side of the cell. The probe was not disconnected during the study. The experiment was completed on two separate days over a seven day period. FIG. 4 plots measured hematocrit values vs . . . reference hematocrit values.

Trial 3

Blood samples were prepared as described previously in connection Trial 2. The samples were introduced into a syringe and sparged with 7%, 14%, and 72% oxygen gas in an RNA® tonometer. Instrumentation was identical except for the probe design (see FIG. 5). In this experiment, a reflector-design probe was mounted in a SensiCath device housing. This provided a closed system in which the sample could be maintained at 37° C. during measurements. FIG. 6 is a table showing actual hematocrit values and calculated hematocrit values that were obtained in accordance with the invention.

Architecture

Figure 7:
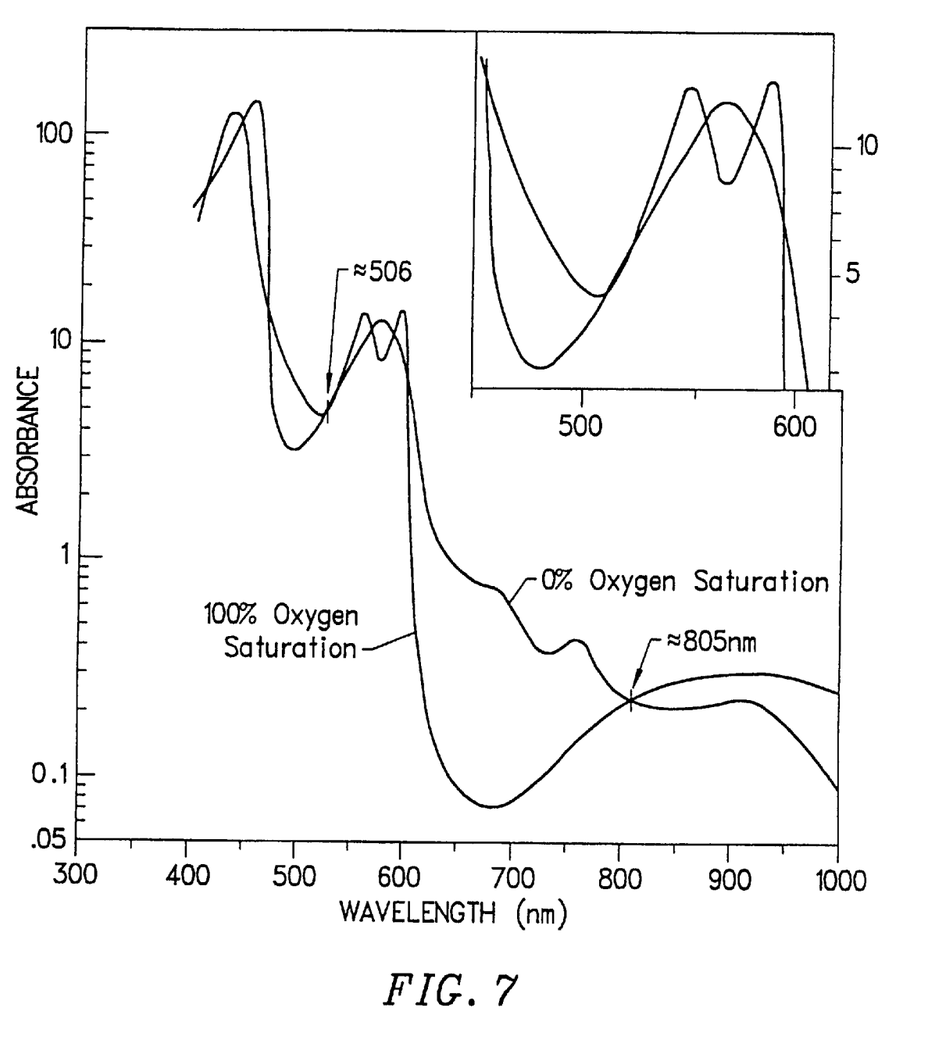
FIG. 7 is a graph plotting wavelength vs . . . absorbance for hemoglobin having 0% oxygen saturation and for hemoglobin having 100% oxygen saturation.

FIG. 7 is a graph plotting wavelength vs . . . absorbance for hemoglobin having 0% oxygen saturation and for hemoglobin having 100% oxygen saturation (source: P. Byrne, O. Clark, PCT Publication, WO 9/01678 (Feb. 21, 1991, FIG. 1b)). It can be seen in FIG. 7 that there is a pronounced convergence of the two plots at the isobestic wavelengths of 506 nm and 805 nm, indicating that oxygen saturation level does not adversely affect absorbance at these wavelengths. A system implementing the invention is preferably designed to detect absorbance at these wavelengths, thus eliminating the effects of variable blood oxygenation on light absorption. One simple flow cell detector is shown in FIG. 1.

Figure 5:
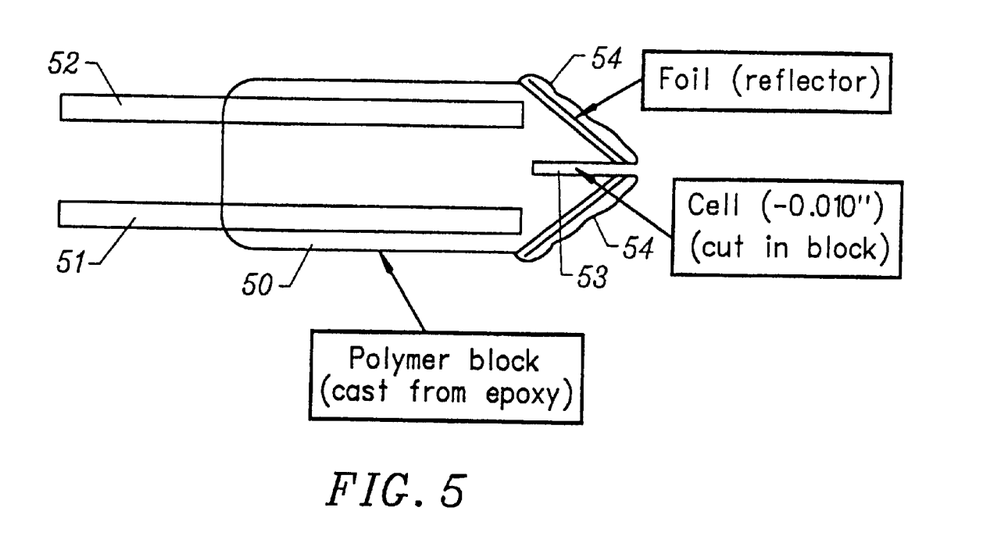
FIG. 5 is a schematic representation of a sensor design according to the invention.
Figure 6:
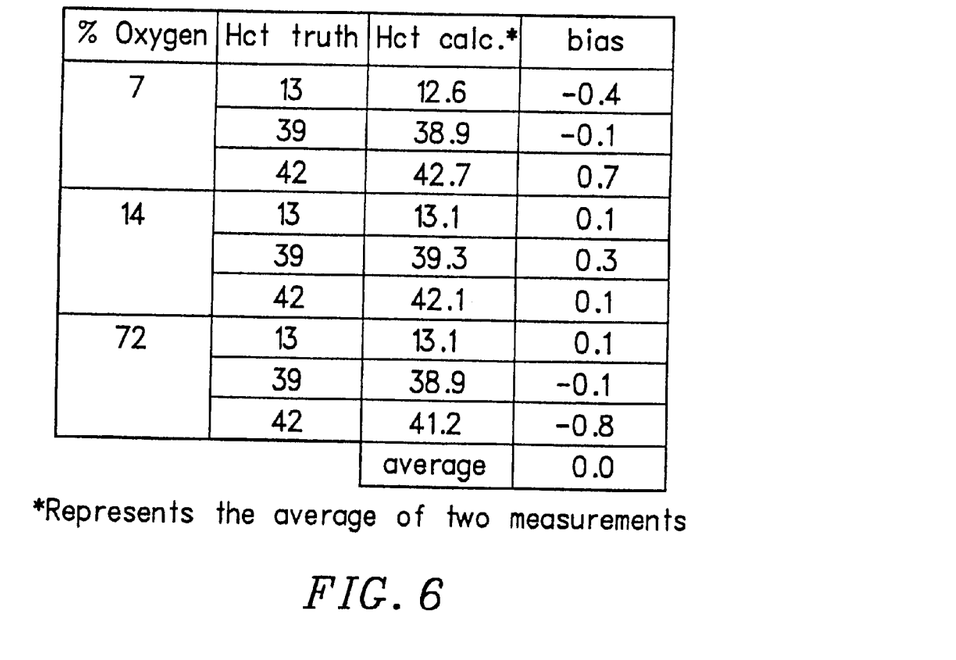
FIG. 6 is a table showing actual hematocrit values and calculated hematocrit values that were obtained in accordance with the invention.

FIG. 5 (discussed above) is a schematic representation of a sensor design in which a polymer block 40 is cast from epoxy such that it includes two fiber optic fibers 51/52. The cell portion 53 of the detector is cut into the epoxy block, and a foil reflector 54 is placed on the outside of the detector. This embodiment of the invention provides a cell having a very narrow cell path, i.e. ~0.010", such that the value of R may essentially equal one.

Figure 8:
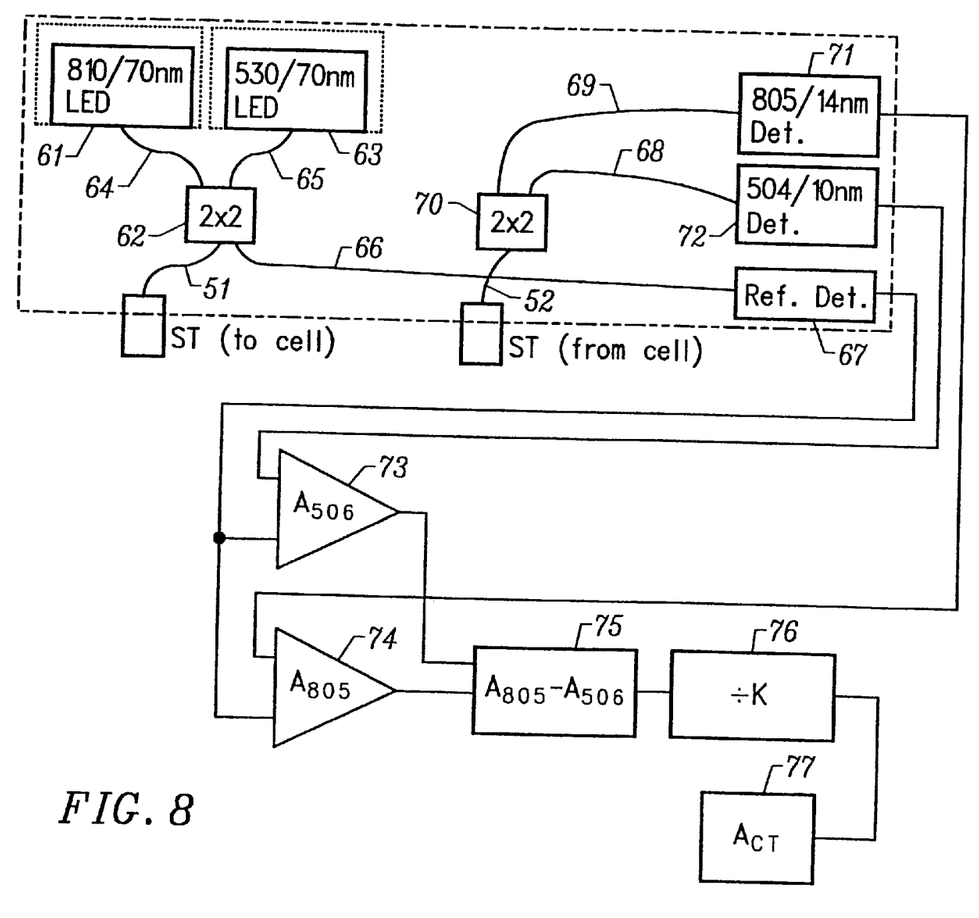
FIG. 8 is a block schematic diagram of an instrument architecture for determining hematocrit according to the invention.

FIG. 8 is a block schematic diagram of an instrument architecture for determining hematocrit according to the embodiment of the invention, for example as expressed in connection with Equations (3) and (5). The architecture may be used in connection with a cell of the type shown in FIGS. 1, 3 or 5. An LED 61 having an emission wavelength of 810/70 nm is coupled to a multiplexer 62 by a fiber 63. Another LED 64 having an emission wavelength of 514/20 nm is coupled to the multiplexer 62 by a fiber 65. A fiber 51 directs the combined light source to a flow cell. A fiber 66 is also coupled to a reference detector 67 to provide a reference value for the light source which is used as a basis for determining sample absorbance. Light passing through the sample in the cell is coupled through a fiber 52 to a second multiplexer 70, where it is thence conducted along a fiber 69 to an 805/14 nm detector 71, and where it is conducted along a fiber 68 to a 504/10 nm detector 72.

The detected reference light value is subtracted from the detected light values at 506 nm and 805 nm at subtraction circuits 73 and 74, respectively, to provide absorbance values at these wavelengths. The absorbance value at 506 nm is subtracted from the absorbance value at 805 nm by a subtractor 75. The resulting value is then divided at a divider 76 by a value K which represents the flow cell constant. The resulting value is the hematocrit value which is displayed on a display 77.

It will be appreciated that the above system architecture is readily implemented using either hardware, software, or a combination thereof, as is readily recognized by those skilled in the art. Further, for those cells where the value R is not equal to one, an alternative algorithm may be implemented in accordance with the equations described above, e.g. Equation (3).

Although the invention is described herein with reference to the preferred embodiment, one skilled in the art will readily appreciate that other applications may be substituted for those set forth herein without departing from the spirit and scope of the present invention. Accordingly, the invention should only be limited by the claims included below.

We claim:

1. A method for determining hematocrit of a blood sample, comprising the steps of:
    measuring absorbance of said blood sample at a first isobestic wavelength;
    measuring absorbance of said blood sample at a second isobestic wavelength; and
    determining hematocrit of said blood sample in accordance with the algorithm:

$$Hct=(T_{i,1}-R^*T_{i,2})/(K_1-R^*K_2),$$

wherein:
    $T_i$ is total absorbance at an isobestic wavelength;
    K is a constant that includes a molar extinction coefficient Hb at that wavelength, a red blood cell scattering factor, and path length;
    Hct is hematocrit; and
    R is the ratio of light scattering from a plasma component measured at two wavelengths.

2. The method of claim 1, wherein said isobestic wavelengths can be any combination of 430 nm, 460 nm, 506 nm, 550 nm, 570 nm and 805 nm, and wherein to simplify the algorithm to achieve desired accuracy of the paired wavelength selected are 506 nm and 805 nm, respectively.

3. The method of claim 1, said determining step further comprising:
    combining K1 and K2 into a constant K, wherein said algorithm comprises:
    Hematocrit=(Absorbance805 nm−Absorbance506 nm)/ K,
    wherein K is the cell constant for a probe used to perform said measurement steps.

4. The method of claim 1, wherein said method determines hematocrit of a blood sample without performing in vitro or in vivo calibration.

5. The method of claim 1, wherein said measuring steps are performed with a measurement probe which comprises a light transmitting optical fiber, a light receiving optical fiber, a measurement cell, and optical filters for wavelengths 805 nm and 506 nm.

6. The method of claim 1, wherein such measuring steps are performed in a probe having a cell with a pathlength of about 0.010".

7. An apparatus for determining hematocrit of a blood sample, comprising:
    a first detector for measuring absorbance of said blood sample at a first isobestic wavelength;
    a second detector for measuring absorbance of said blood sample at a second isobestic wavelength; and
    means for determining hematocrit of said blood sample in accordance with the algorithm:

$$Hct=(T_{i,1}-R^*T_{i,2})/(K_1-R^*K_2),$$

wherein:
    $T_i$ is total absorbance at an isobestic wavelength;
    K is a constant that includes a molar extinction coefficient Hb at that wavelength, a red blood cell scattering factor, and path length;
    Hct is hematocrit; and
    R is the ratio of light scattering from a plasma component measured with two wavelengths.

8. The apparatus of claim 7, wherein said isobestic wavelengths are 506 nm and 805 nm, respectively.

9. The apparatus of claim 8, said determining means combining K1 and K2 into a constant K, wherein said algorithm comprises:

Hematocrit=(Absorbance805 nm−Absorbance506 nm)/K, wherein K is a cell constant for a probe that provides said first detector and said second detector.

10. The apparatus of claim 9, wherein said probe comprises:
    a light transmitting optical fiber;
    a light receiving optical fiber;
    a measurement cell; and
    optical filters for wavelengths 805 nm and 506 nm.

11. The apparatus of claim 7, wherein said apparatus determines hematocrit of a blood sample without performing in vitro or in vivo calibration.

12. The apparatus of claim 7, wherein said first detector and said second detector are provided in a probe having a cell with a pathlength of about 0.010".

13. An apparatus for determining hematocrit of a blood sample, comprising:

a first detector for measuring absorbance of said blood sample at an isobestic wavelength of 506 nm;

a second detector for measuring absorbance of said blood sample at an isobestic wavelength of 805 nm; and means for determining hematocrit of said blood sample in accordance with the algorithm:

$$\text{Hematocrit} = (\text{Absorbance}_{805\,nm} - \text{Absorbance}_{506\,nm})/K,$$

wherein K is a cell constant for a probe that provides said first detector and said second detector.

14. The apparatus of claim 13, further comprising:

a first light source having an emission wavelength between about 800 to 815 nm; and a second light source having an emission wavelength between about 504 to 510 nm.

15. The apparatus of claim 14, further comprising:

a reference detector for detecting first and second light source emissions before said light source emissions pass through said blood sample.

16. The apparatus of claim 15, further comprising:

means for subtracting a detected reference light value from detected light values at 506 nm and 805 nm to provide absorbance values at these wavelengths.

17. The apparatus of claim 13, wherein said first detector and said second detector are provided in a probe having a cell with a pathlength of about 0.010".

18. A method for determining hematocrit of a blood sample, comprising the steps of:

measuring absorbance of said blood sample at an isobestic wavelength of 506 nm;

measuring absorbance of said blood sample at an isobestic wavelength of 805 nm; and determining hematocrit of said blood sample in accordance with the algorithm:

$$\text{Hematocrit} = (\text{Absorbance}_{805\,nm} - \text{Absorbance}_{506\,nm})/K,$$

wherein K is a cell constant for a probe that provides said first detector and said second detector.

19. The method of claim 18, further comprising the steps of:

providing a first light source having an emission wavelength between about 800 to 815 nm; and providing a second light source having an emission wavelength between about 504 to 510 nm.

20. The method of claim 19, further comprising the step of:

providing a reference detector for detecting first and second light source emissions before said light source emissions pass through said blood sample.

21. The method of claim 18, wherein said measuring steps are performed in a probe having a cell with a pathlength of about 0.010".

* * * * *